United States Patent [19]
Gree et al.

[11] Patent Number: 5,599,975
[45] Date of Patent: Feb. 4, 1997

[54] NEW CYCLISED ANALOGUES OF FATTY ACID METABOLITES

[75] Inventors: René Gree, Cesson-Sevigne; Ali M. Hachem, Rennes; Danielle Gree, Cesson-Sevigne; Yves Le Floc'h, Betton; Yves Rolland, Vanves; Serge Simonet, Conflans St-Honorine; Tony Verbeuren, Vernouillet, all of France

[73] Assignee: Adir Et Compagnie, Courbevoie, France

[21] Appl. No.: 330,027

[22] Filed: Oct. 27, 1994

[30] Foreign Application Priority Data

Oct. 28, 1993 [FR] France .................................. 93 12858

[51] Int. Cl.⁶ ..................................................... C07C 59/00
[52] U.S. Cl. .......................... 562/465; 562/621; 546/335; 558/194; 568/442; 568/322; 560/55; 564/161; 564/182; 564/226
[58] Field of Search ..................................... 562/465, 621; 560/55; 564/161, 182, 226; 568/442, 322; 558/194; 546/335; 514/532, 545, 570

[56] References Cited

FOREIGN PATENT DOCUMENTS 085959 8/1983 European Pat. Off. .
4009117 9/1991 Germany .

*Primary Examiner*—Paul J. Killos
*Attorney, Agent, or Firm*—The Firm of Gordon W. Hueschen

[57] ABSTRACT

A compound selected from those of formula (I):

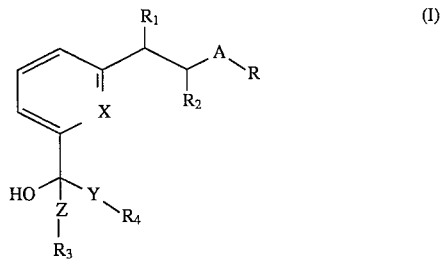

wherein A, X, Y, Z, R, $R_1$, $R_2$, $R_3$ and $R_4$ are as defined in the description.

This compound or its physiologically tolerable salts may be used therapeutically as platelet anti-aggregation agent.

9 Claims, No Drawings

NEW CYCLISED ANALOGUES OF FATTY ACID METABOLITES

The present invention relates to new analogues of fatty acid metabolites, a process for their preparation, and pharmaceutical compositions containing them.

Recent studies (M. R. Buchanan et al., A.A.S., 37, 273–281, (1992)) show that the intracellular production of metabolites of the lipoxygenase pathway, 13-hydroxyoctadecadienoic acid (13-HODE, linoleic acid metabolite) and 15-hydroxy-eicosatetraenoic acid (1 5-HETE, arachidonic acid metabolite) regulates the adhesive properties of those cells.

It may be concluded from that that the 13-HODE/15-HETE ratio is closely related to the ability of malignant cancer cells to adhere to endothelial cells, probably by interfering with the expression of the vitronectine receptor. In the same way, these metabolites of the lipoxygenase pathway seem to be implicated in the expression of the platelet glycoprotein IIB/IIIA, the fibrinogen receptor, which is the final link in the platelet aggregation process. Lipoxygenase metabolites also interfere with the platelet receptor for thromboxane, to which they present an antagonist-type activity (M. Croset et al., Biochem. Pharm., (37) 7, 1275–1280, (1988)).

The applicant has discovered new analogues of fatty acid metabolites that exhibit very valuable properties when used in adhesion pathologies and in particular in platelet aggregation phenomena and in cancer.

The invention relates more specifically to new analogues of fatty acid metabolites corresponding to formula (I):

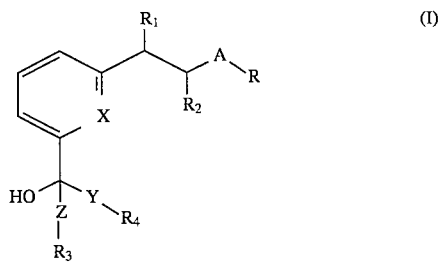

wherein:

A represents a divalent hydrocarbon radical having from 2 to 10 carbon atoms inclusive in straight or branched chain and optionally containing one or more unsaturations in the form of double and/or triple bonds, R is selected from halogen, selected from fluorine, chlorine, bromine and iodine, —OR', —COOR', —COR', P(O)(OR')$_2$, —CH=N—OR', —CONHR', —CH=NR", —CH=NAr, NHSO$_2$Ar, —CON(OH)R', —NHR', —NHCOR', —CH=N—NHAr,

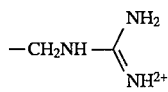

and optionally substituted imidazolyl, pyrazolyl or tetrazolyl,

R' is selected from hydrogen and straight-chain or branched alkyl having from 1 to 6 carbon atoms inclusive, R" represents straight-chain or branched alkyl having from 1 to 6 carbon atoms inclusive, Ar represents optionally substituted aryl selected from phenyl and naphthyl, R$_1$ and R$_2$ each represents hydrogen or together form a bond, R$_3$ is selected from hydrogen and alkyl having from 2 to 10 carbon atoms inclusive in straight or branched chain, R$_4$ represents a hydrocarbon radical having from 2 to 10 carbon atoms inclusive in straight or branched chain and optionally containing one or more unsaturations in the form of double and/or triple bonds, X is selected from CH and nitrogen, Y and Z each represents, independently of the other, a valency bond or para-phenylene, it being understood that the expression "optionally substituted" indicates that the radical concerned may optionally be substituted by one or more groups selected from chlorine, fluorine, bromine, iodine, amino, alkylamino, dialkylamino, nitro, cyano, alkyl, alkoxy, acyl, acyloxy, carboxy, alkoxycarbonyl, amido and carboxamido, their stereoisomers, their possible N-oxides, and also their pharmaceutically acceptable addition salts with an acid or a base.

The present invention relates also to a process for the preparation of compounds of formula (I) which is characterised in that the aldehyde functions of the compound of formula (II):

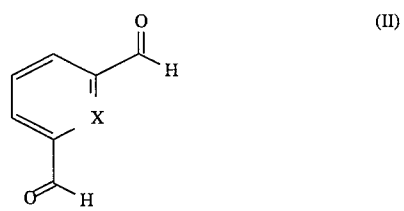

wherein X is as defined for formula (I) are protected by methyl orthoformate, at room temperature, in an anhydrous alcoholic solvent, such as anhydrous methanol, in the presence of an ammonium salt, such as ammonium nitrate, to obtain the bis-acetal of formula (III):

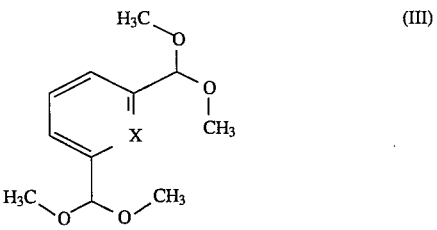

wherein X is as defined above, which is converted into an acetal-aldehyde of formula (IV):

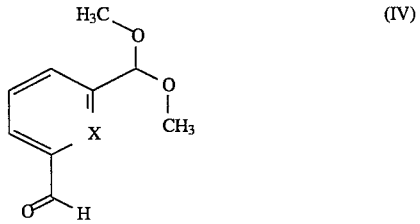

wherein X is as defined above,
by the action of an aqueous sulfuric acid solution in an organic solvent, such as dichloromethane, in the presence of silica,
which compound of formula (IV):
A)
when the group Y defined in formula (I) represents a bond and the radical R$_4$ of the same desired compound of formula (I) contains one or more unsaturations (that radical hereinafter being denoted as R$_4$A),
is reacted with trimethylsulfonium methyl sulfate, in the presence of an aqueous sodium hydroxide solution, in a solvent, such as dichloromethane, at room temperature, to obtain the epoxide of formula ($V_A$):

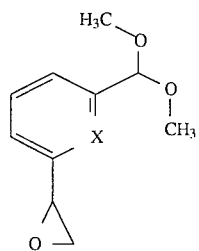

wherein X is as defined above,
which, placed in contact with a compound of formula (VI):

H—$R_{5A}$ (VI)

wherein $R_{5A}$ is such that —$R_{4A}$ is —$CH_2$—$R_{5A}$ where $R_{4A}$ is as defined above,
having reacted beforehand with a solution of butyllithium in hexane in the presence of a chelator for cations, such as hexamethylphosphoric triamide (HMPA), in an anhydrous polar solvent, such as tetrahydrofuran, at 0° C., yields the compound of formula ($VI_A$):

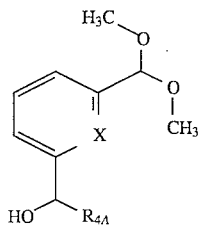

wherein X and $R_{4A}$ are as defined above,
or:
B)
when the group Y of the compound of formula (I) represents a bond and the radical $R_4$ of the same desired compound of formula (I) represents a saturated hydrocarbon group (that radical hereinafter being denoted as $R_{4B}$), is reacted with the Grignard reagent of formula ($V_B$):

$R_{5B}$—Mg—Hal ($V_B$)

wherein $R_{5B}$ is such that $R_{4B}$ is —$CH_2$—$R_{5B}$ where $R_{4B}$ is as defined above, and Hal is a halogen atom, such as bromine,
in anhydrous tetrahydrofuran, at a temperature of –50° C., to yield the compound of formula ($VI_B$):

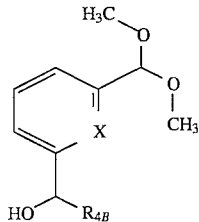

wherein X is as defined for formula (I) and $R_{4B}$ is as defined for formula ($V_B$),
or:

C)
when the group Y of the compound of formula (I) represents a para-phenylene group, is reacted with the compound of formula ($V_C$):

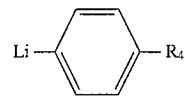

wherein $R_4$ is as defined above,
in anhydrous tetrahydrofuran, at a temperature of –50° C., to yield the compound of formula ($VI_C$):

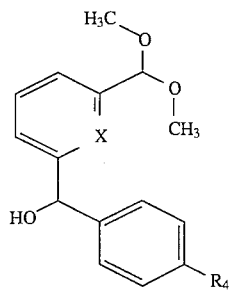

wherein X and $R_4$ are as defined above,
the totality of the compounds of formulae ($VI_A$), ($VI_B$) and ($VI_C$) forming the totality of the compounds of formula (VI):

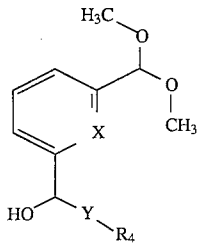

wherein X, Y and $R_4$ are as defined above,
which may, if desired, be subjected to an oxidation reaction, by a mixture of oxalyl chloride and dimethyl sulfoxide, in a chlorinated solvent, such as dichloromethane, in order to obtain the compound of formula (VII):

(VII)

wherein X and $R_4$ are as defined above,
which is
either:
A) treated with a reagent of formula ($VIII_A$):

Li—$R'_3$ ($VIII_A$)

wherein $R'_3$ represents an alkyl radical containing from 2 to 10 carbon atoms in straight or branched chain,
under the same conditions as the compound of formula ($V_B$), to yield the compound of formula ($IX_A$):

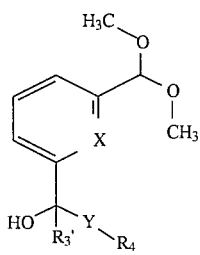
(IX$_A$)

wherein R'$_3$, R$_4$, X and Y are as defined above,
or:
B) treated with a reagent of formula (VIII$_B$):

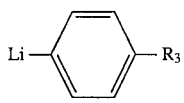
(VII$_B$)

wherein R$_3$ is as defined above,
under the same conditions as those used to obtain the compound of formula (VI$_C$), to yield the compound of formula (IX$_B$):

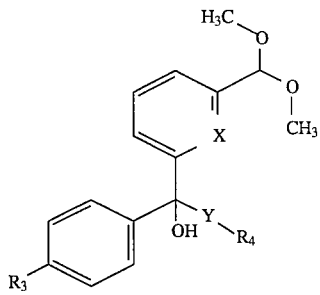
(IX$_B$)

wherein R$_3$, R$_4$, X and Y are as defined above,
the totality of the compounds of formulae (VI), (IX$_A$) and (IX$_B$) forming the totality of the compounds of formula (IX):

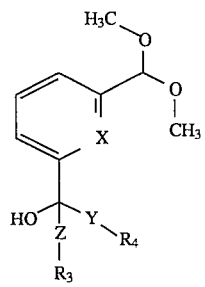
(IX)

wherein R$_3$, R$_4$, X, Y and Z are as defined above,
the alcohol function of which compounds of formula (IX) is protected by tert-butyldiphenylsilyl chloride, in the presence of imidazole, in a solvent, such as dimethylformamide, at room temperature, to yield the compound of formula (X):

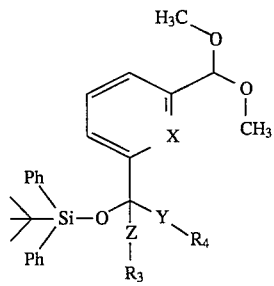
(X)

wherein X, Y, Z, R$_3$ and R$_4$ are as defined above, the acetal function of the compound of formula (X) then being converted in a manner identical to that used for the compound of formula (III) into an aldehyde of formula (XI):

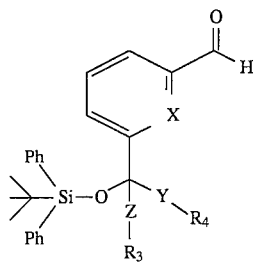
(XI)

wherein X, Y, Z, R$_3$ and R$_4$ are as defined above,
which is then subjected to a Wittig reaction with a compound of formula (XII):

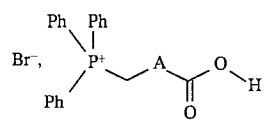
(XII)

wherein A is as defined above,
dissolved beforehand in an anhydrous solvent, such as tetrahydrofuran, in the presence of lithium bis(trimethylsilyl)amide and of hexamethylphosphoric triamide (HMPA), at a temperature of −80° C., to yield the compound of formula (XIIIa):

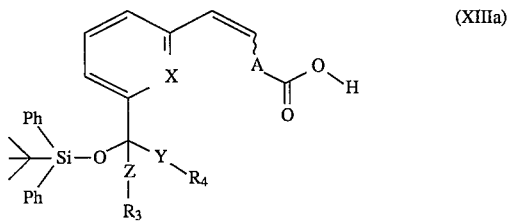
(XIIIa)

wherein A, X, Y, Z, R$_3$ and R$_4$ are as defined above,
which, if desired, may be converted in accordance with a conventional method of esterification into a compound of formula (XIIIb):

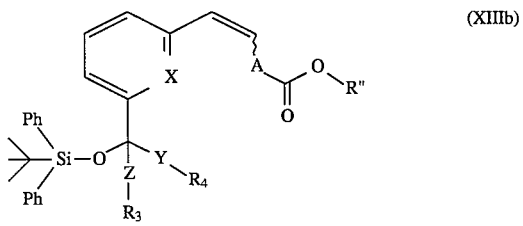
(XIIIb)

wherein A, X, Y, Z, R", R$_3$ and R$_4$ are as defined above, the corresponding Z and E isomers of which compounds of formulae (XIIIa) and (XIIIb) are separated on a silica column, then optionally subjected to a reaction for the deprotection of the alcohol function, by the action of a tetraalkylammonium fluoride, such as tetrabutylammonium fluoride, in a polar solvent, such as tetrahydrofuran, at 0° C., to yield the alcohols of formulae (XIVa) and (XIVb) respectively:

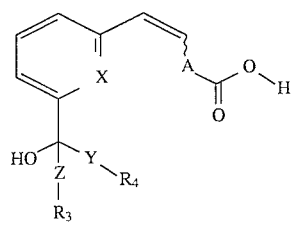
(XIVa)

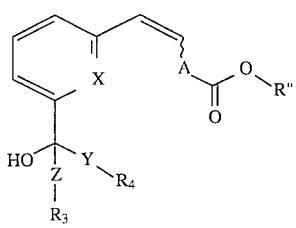
(XIVb)

wherein A, X, Y, Z, R", $R_3$ and $R_4$ are as defined above, the compound of formula (XIVa) then optionally being converted, after temporary protection of the alcohol function, into the amide of formula (XIVc):

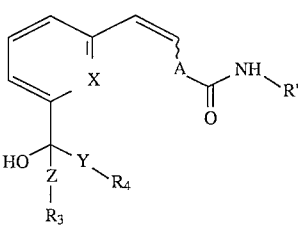
(XIVc)

wherein A, X, Y, Z, R', $R_3$ and $R_4$ are as defined above, it also being possible for the ester of formula (XIIIb) to be hydrolysed directly in accordance with the method described for obtaining the acid of formula (XIVa), then optionally converted into its acyl chloride of formula (XIV):

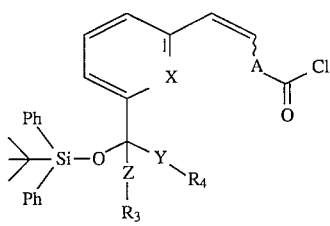
(XIV)

wherein A, X, Y, Z, $R_3$ and $R_4$ are as defined above, by the action of oxalyl chloride in the presence of N,N-dimethylformamide in tetrahydrofuran, at 0° C., which acyl chloride of formula (XIV) is immediately treated with an N-alkylhydroxylamine hydrochloride of formula (XV):

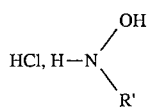
(XV)

wherein R' is as defined above,
in basic medium at 0° C. to yield, after freeing the alcohol function, the hydroxamic acid of formula (XIVd):

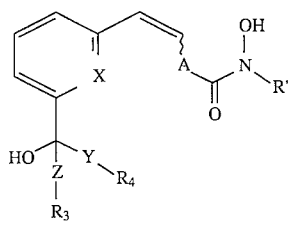
(XIVd)

wherein A, X, Y, Z, R', $R_3$ and $R_4$ are as defined above it also being possible for the acyl chloride of formula (XIV) to be treated immediately with a hydrazine of formula $H_2N$-NHAr, wherein Ar is as defined above, to yield, after freeing the alcohol function, the corresponding hydrazides of formula (XIVe):

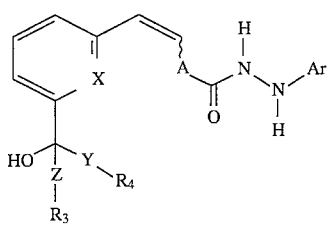
(XIVe)

wherein A, X, Y, Z, Ar, $R_3$ and $R_4$ are as defined above the ester of formula (XIIIb) also leading, according to conventional methods of reduction and after freeing the alcohol protected in the form of silylated ether, to the alcohol and ether of formula (XIVf):

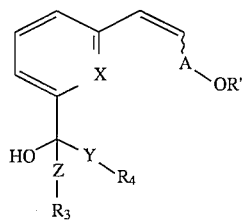
(XIVf)

wherein A, X, Y, Z, R', $R_3$ and $R_4$ are as defined above which in turn lead, after temporary protection of the α-aromatic alcohol function, to the halogenated compounds of formula (XIVg):

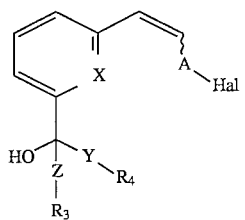
(XIVg)

wherein A, X, Y, Z, $R_3$ and $R_4$ are as defined above and Hal represents a halogen atom selected from fluorine, chlorine, bromine and iodine,
allowing the preparation of phosphonates of formula (XIVh):

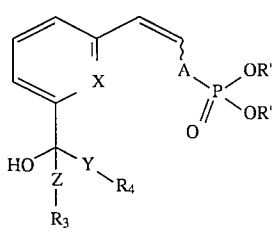
(XIVh)

wherein A, X, Y, Z, R', $R_3$ and $R_4$ are as defined above or, by reaction with a compound of formula (XVI):

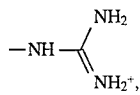
(XVI)

wherein $B_1$ represents the group —NHR", $$-NH-\!\!\!<\!\!\!\begin{array}{c}NH_2\\NH_2^+\end{array},$$

optionally substituted imidazolyl, optionally substituted pyrazolyl or optionally substituted tetrazolyl, R" being as defined above,
under appropriate and conventional operating conditions, allowing the preparation of compounds of formula (XVIa):

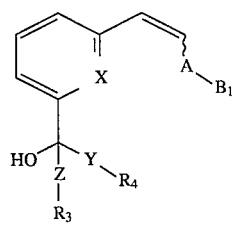
(XVIa)

wherein A, $B_1$, X, Y, Z, $R_3$ and $R_4$ are as defined above, the amines of formula (XVIb):

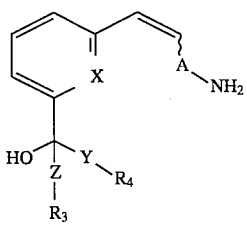
(XVIb)

wherein A, X, Y, Z, $R_3$ and $R_4$ are as defined above,
then being obtained by preparation of the azide, for example with sodium azide, starting from the halogenated precursor compound of formula (XIVg), then hydrogenation of that azide, for example by means of triphenylphosphine and water,
which amines of formula (XVIb) may be converted by the action of a compound of formula (XVI'):

Hal—$B_2$ (XVI')

wherein $B_2$ represents —$SO_2Ar$ or —COR' and Hal, Ar and R' are as defined above, into compounds of formula (XVIc):

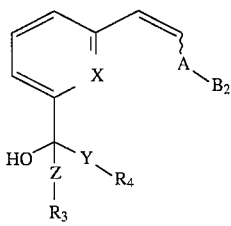
(XVIc)

wherein A, $B_2$, X, Y, Z, $R_3$ and $R_4$ are as defined above, the totality of the compounds of formulae (XVIa), (XVIb) and (XVIc) forming the totality of the compounds of formula (XIVi):

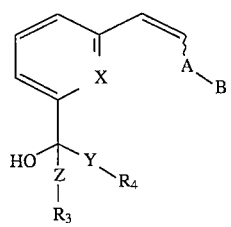
(XVIi)

wherein A, X, Y, Z, $R_3$ and $R_4$ are as defined above and B represents $B_1$, $B_2$ or the group $NH_2$,
it also being possible for the ester of formula (XIIIb) to be:
1/- hydrolysed to the corresponding acid then treated with a compound of formula Li—R", wherein R" is as defined above, to yield, after freeing the alcohol function protected until then in the form of a silylated ether, the ketones of formula (XIVj):

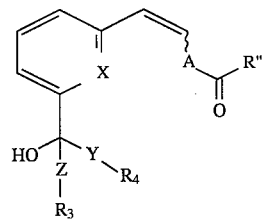
(XVIj)

wherein A, X, Y, Z, R", $R_3$ and $R_4$ are as defined above,
2/ - treated with an equivalent of diisobutylaluminium hydride (DIBAL) at reduced temperature to yield, after freeing the alcohol function, the aldehydes of formula (XIVk):

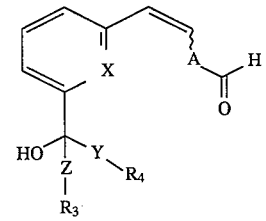
(XVIk)

wherein A, X, Y, Z, $R_3$ and $R_4$ are as defined above,
it being possible for those aldehydes of formula (XIVk) to be:
either:
α) treated with hydroxylamine to yield the oximes of formula (XIVl):

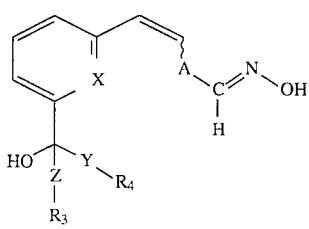
(XIVl)

wherein A, X, Y, Z, R₃ and R₄ are as defined above, it being possible for the oximes of formula (XIVl) in turn to be alkylated to compounds of formula (XIVm):

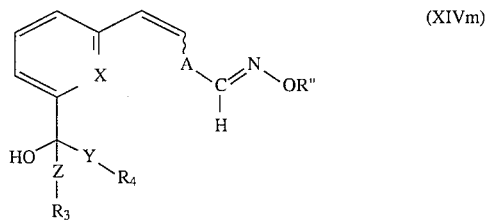
(XIVm)

wherein A, X, Y, Z, R", R₃ and R₄ are as defined above, by a reagent of formula W—R" wherein W represents a leaving group, such as halogen or a sulfate group, and R" is as defined above,
or:

β) treated with an amine of formula Hhd 2N—R", wherein R" is as defined above, to yield the imines of formula (XIVn):

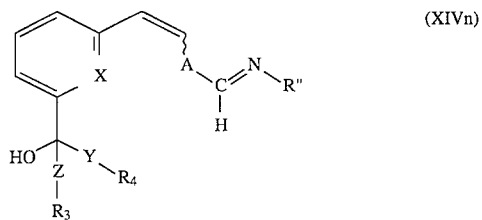
(XIVn)

wherein A, X, Y, Z, R", R₃ and R₄ are as defined above, the totality of the compounds of formulae (XIVa) to (XIVn) forming the totality of the compounds of formula (XVII):

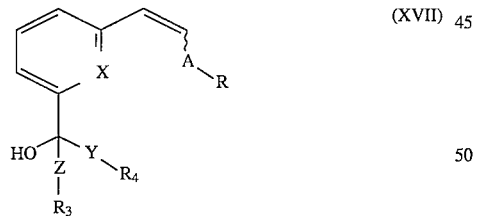
(XVII)

wherein A, X, Y, Z, R, R₃ and R₄ are as defined above, which, optionally subjected to hydrogenation according to a conventional method, for example a catalytic method using palladium, result in compounds of formula (XVIII):

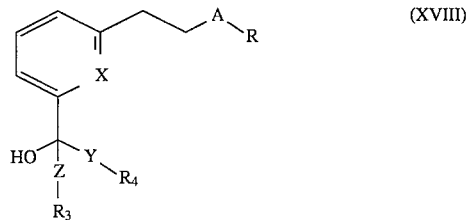
(XVIII)

wherein A, X, Y, Z, R, R₃ and R₄ are as defined above, the totality of the compounds of formulae (XVII) and (XVIII) forming the totality of the compounds of formula (I) which, where appropriate, are purified according to a conventional method of purification and, if desired, separated into their isomers by a conventional method of separation, and which are optionally converted into their N-oxides and/or their pharmaceutically-acceptable addition salts with an acid or a base.

The compounds of formula (I) wherein X represents a nitrogen atom may also be prepared from 2,6-dimethanolpyridine, one of the alcohol functions of which is protected by tert-butyldiphenylsilyl chloride to obtain the compound of formula (XIX):

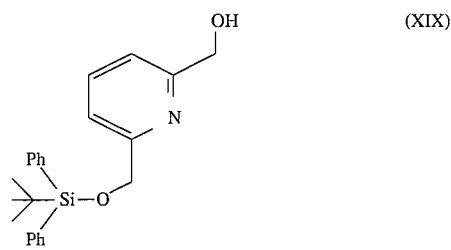
(XIX)

which is then oxidised, for example by a mixture of oxalyl chloride and dimethyl sulfoxide in dichloromethane, to the aldehyde of formula (XX):

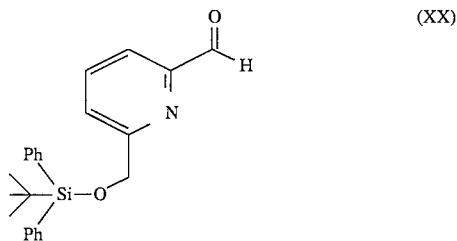
(XX)

which is then subjected to the Wittig reaction described for obtaining the compound of formula (XIIIb) in order to yield the compound of formula (XXI):

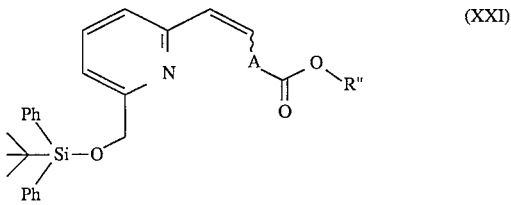
(XXI)

wherein A and R" are as defined above,
the alcohol function of which is deprotected in accordance with the method used to obtain the compound of formula (XIVa), then oxidised to an aldehyde in accordance with the method described for the compound (XVIII), thus leading to the compound of formula (XXII):

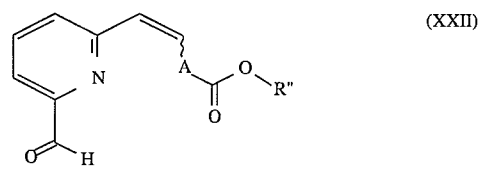
(XXII)

wherein A and R" are as defined above,
which is then treated in a manner analogous to that of the compound of formula (IV), in accordance with the meanings of Y and R₄, to yield the compounds of formula (XXIII):

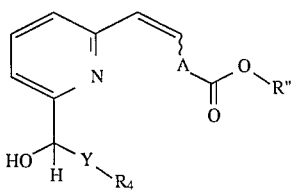

(XXIII)

wherein A, Y, R" and R₄ are as defined above,
which are then optionally treated in a manner analogous to that of compounds of formula (VI) in order to obtain compounds of formula (XXIV):

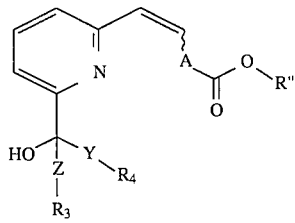

(XXIV)

wherein A, Y, Z, R", R₃ and R₄ are as defined above,
the ester function of which is optionally modified in a manner identical to the methods used to obtain compounds (XIVa) to (XIVn) to yield compounds of formula (XXV):

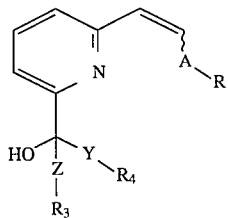

(XXV)

wherein A, Y, Z, R, R₃ and R₄ are as defined above,
which are optionally subjected to hydrogenation in accordance with the method described for the hydrogenation of compounds of formula (XVII) to obtain compounds of formula (XXVI):

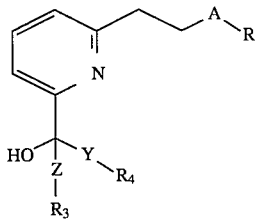

(XXVI)

wherein A, Y, Z, R, R₃ and R₄ are as defined above,
the totality of the compounds of formulae (XXV) and (XXVI) forming the totality of the compounds of formula (XXVII):

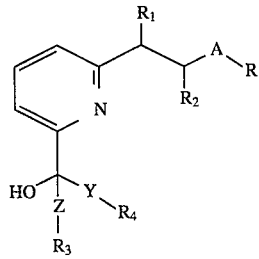

(XXVII)

wherein A, R, R1, R₂, R₃, R₄, Y and Z are as defined above, a particular instance of the compounds of formula (I) wherein X represents nitrogen.

The compounds in which the radical A, R₄ or R₃ contains one or more double bonds may advantageously be obtained from their respective precursors in which A, R₄ or R₃ contains triple bonds. Those compounds are obtained by catalytic hydrogenation, for example with hydrogen and Lindlar catalyst, at any stage of the synthesis considered appropriate by the person skilled in the art.

The aldehydes of formula (XIVk) may also be obtained from alcohols of formula (XXVIII):

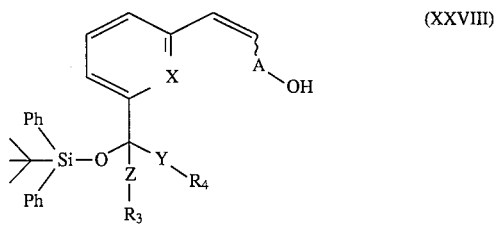

(XXVIII)

wherein A, X, Y, Z, R₃ and R₄ are as defined above,
by the action of an oxidising agent, such as pyridinium chlorochromate in the presence of sodium acetate in methylene chloride.

The compounds of the invention surprisingly exhibit very significant platelet antiaggregation properties. The compounds thus have an especially beneficial action in disorders involving a platelet aggregation process. The novel compounds may therefore be used for treating disorders resulting from or associated with platelet adhesion pathologies and especially for treating thromboembolism, by dissolving the blood clots, pulmonary embolism, arterial embolism of the extremities, myocardial infarct, arteriosclerosis and malignant cancer, as well as for maintaining blood homeostasis, in particular in extracorporeal circulation.

They may also be used as agents for preventing the extension of the thrombotic process by using them as anticoagulants with a direct and rapid action.

The present invention relates also to pharmaceutical compositions comprising a compound of formula (I), or a pharmaceutically acceptable addition salt thereof with an acid or a base, alone or in combination with one or more inert non-toxic excipients. Among the pharmaceutical compositions according to the invention there may be mentioned more especially those suitable for oral, parenteral, nasal, rectal, perlingual, ocular or pulmonary administration, and especially injectable preparations, aerosols, eye or nose drops, tablets, film-coated tablets, dragées, soft gelatin capsules, suppositories, hard gelatin capsules, creams, ointments, dermal gels . . .

The useful dosage varies in accordance with the age and weight of the patient, the route of administration, the nature of the disorder and of possible associated treatments and ranges from 0.5 mg to 2 g per 24 hours.

The following Examples illustrate the invention without, however, limiting the invention in any way.

15

The starting materials are readily available or are prepared using known methods of operation.

PREPARATION A:

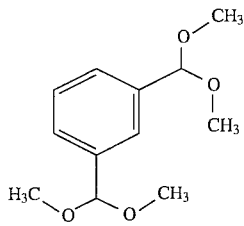

25 g of isophthalaldehyde (180 mmols), 78 g of methyl orthoformate (4 equivalents), 250 ml of anhydrous methanol and then 600 mg of ammonium nitrate are introduced into a flask. The mixture is refluxed for 2 hours, then the methanol is evaporated off in vacuo, the residues are dissolved in ether and the ammonium nitrate is removed by filtration. The ether is removed again under reduced pressure and the bis-acetal is purified by distillation, yielding 38 g (167.4 mmols) of a colourless oil corresponding to the expected product.

Yield: 93% Boiling temperature: 118° C. (3 mm Hg)

PREPARATION B:

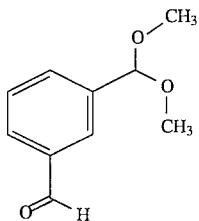

40 g of silica are suspended in 140 ml of dichloromethane to which 15 drops of an aqueous sulfuric acid solution (1% by weight) are added. 10 g of the bis-acetal from Preparation A are then added and the mixture is stirred vigorously at room temperature for 45 minutes and then filtered. The solvents are then evaporated off under reduced pressure and the crude product is purified by chromatography on a silica column (eluent: ether/petroleum ether, 20:80 with 1% triethylamine). 7 g of the expected acetal-aldehyde are obtained in the form of a colourless oil.

Yield: 88%

PREPARATION C:

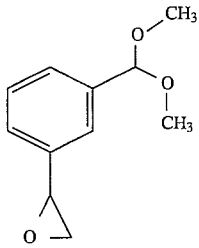

7 g (38.8 mmols) of the acetal-aldehyde obtained in Preparation B are dissolved in 70 ml of dichloromethane. 16 g (85.0 mmols) of trimethylsulfonium methyl sulfate, then 35 ml of an aqueous solution of sodium hydroxide (50% by weight) are added to the mixture. After stirring vigorously at room temperature for 4 h, the reaction mixture is extracted with dichloromethane. After customary treatment of the organic phase, the crude product is purified by chromatography on a silica column (eluent: ether/petroleum ether, 20:80 with 1% triethylamine). 6.5 g of a colourless oil corresponding to the expected epoxide are obtained.

Yield: 85%

16

EXAMPLE 1

1-[(1Z)-5-methoxycarbonylpent-1-enyl]-3-(1-hydroxynon-3-ynyl)benzene

Step 1a:
1-dimethoxymethyl-3-(1-hydroxynon-3-ynyl)benzene 19 ml (47.5 mmols) of a 2.5M butyllithium solution in hexane are added dropwise at 0° C., under nitrogen and with magnetic stirring, to 8.6 ml of hept-1-yne (65.5 mmols) dissolved in 30 ml of anhydrous tetrahydrofuran. After the mixture has been stirred for 15 min at 0° C., 30 ml of hexamethylphosphoric triamide (HMPA) are added and then, slowly, 4.7 g (24.2 mmols) of the epoxide obtained in Preparation C, dissolved in 35 ml of tetrahydrofuran. The whole is left to return to room temperature. After customary treatment of the organic phase, the crude product is purified by chromatography on a silica column (eluent: ether/petroleum ether, 50:50 with 1% triethylamine). 6.8 g of a colourless oil corresponding to the expected alcohol are collected.

Yield: 97%.

Step 1b: Protection of the Alcohol Function 3.5 g (51.4 mmols) of imidazole, followed by 6.4 ml (24.6 mmols) of diphenyl-tert-butylsilyl chloride, are then added, under nitrogen and with magnetic stirring, to 6 g (20.7 mmols) of the alcohol obtained in Step 1a dissolved in 100 ml of anhydrous dimethylformamide. After 24 hours' stirring at room temperature, the mixture is hydrolysed with a 2% aqueous sodium hydrogen carbonate solution. The treatment of the organic phases yields a crude product which is purified by chromatography on a silica column (eluent: ether/petroleum ether, 5:95 then 10:90 with 1% triethylamine). 10.7 g of silylated ether are obtained.

Yield: 97%

Step 1c: Deprotection of the Acetal Function 1 ml of a 2.5% by weight aqueous sulfuric acid solution are added to a suspension of 50 g of silica in 100 ml of methylene chloride. The mixture is stirred vigorously for a few minutes and then 10.7 g (20.2 mmols) of the acetal prepared in Step 1b dissolved in 100 ml of dichloromethane are added. After stirring vigorously for 1 h 30, the mixture is filtered, the solvent is evaporated off in vacuo and the crude product is purified by flash chromatography (eluent: ether/petroleum ether, 10:90). 9.6 g of the expected aldehyde are obtained in the form of a colourless oil.

Yield: 98%

Step 1d:
1-[(1Z)-5-methoxycarbonylpent-1-enyl]-3-(1-hydroxynon-3-ynyl)benzene 6.3 g (13.95 mmols) of (4-carboxybutyl)triphenylphosphonium bromide are dried with a pump (3–4 mm Hg) in an oil bath at 80° C., then suspended, under nitrogen, in 200 ml of anhydrous tetrahydrofuran. The mixture is cooled to −10° C. and 4.5 g (27.9 mmols) of lithium bis(trimethylsilyl)amide are added in portions under nitrogen and with magnetic stirring (the solution turns orange then deep red after 20–30 minutes' stirring); the mixture is then cooled to −35° C. for the addition of 19 ml of anhydrous hexamethylphosphoric triamide (HMPA), then to −80° C. for the slow addition of 4.5 g (9.3 mmols) of the aldehyde obtained in Step 1 c in 30 ml of anhydrous tetrahydrofuran. The solution is stirred at −80° C. for 1 h 30 then at −35° C. and 3 g of sodium carbonate and 5.8 g of di... ...ulfate (4.4 ml) are added; the mixture is left to re... room temperature while stirring slowly for 12 hou... ...r hydrolysis with a saturated aqueous solution of a... ...ium chloride, and customary treatment of the organi... ...5.1 g of a mixture of the two isomers (Z/E=80/20) ... ...ained and the isomers are separated by chromatogra... ...n a silica column (eluent: ether/petroleum ether 5:9... ...g (2.93 mmols) of the Z isomer is brought into sol... ...n 50 ml of tetrahydrofuran to which 3.5 ml (3.85 ... ...) of a 1.1M solution of tetrabutylammonium fluor... tetrahydrofuran are added at 0° C. After stirring for ... ...0° C., the mixture is left at room temperature for 14 h ... ...en hydrolysed; the reaction mixture is then extracted w... ...er (3 times) and the organic phases are treated in accor... with the customary method to yield 940 mg of the ... product in the form of a colourless oil.

Yield: 88%

Proton NMR spectrum characteristics: (90 MHz, CDCl$_3$, δ ppm):

7.42–7.08 (m, 4H aromatic); 6.45 (dt, 1H, ArC$\underline{H}$=CH—, J=11.7, 1.7 Hz); 5.63 (dt, 1H, ArC$\underline{H}$=CHCH$_2$—, J=11.6, 7.3 Hz); 4.79 (t, 1H, HOCHC$\underline{H}_2$—, J=6.3 Hz); 3.63 (s, 3H, —CO$_2$C$\underline{H}_3$); 2.71–2.50 (m, 2H, HOCHC$\underline{H}_2$C≡C—); 2.47–2.20 (m, 7H, —C$\underline{H}_2$CO$_2$CH$_3$; —C≡CC$\underline{H}_2$CH$_2$—, ArCH=CHC$\underline{H}_2$— and $\underline{H}$OCH—); 1.95–1.61 (m, 2H, —C$\underline{H}_2$CH$_2$CO$_2$CH$_3$); 1.61–1.13 (m, 6H, —CH$_2$(C$\underline{H}_2$)$_3$CH$_3$); 0.89 (t, 3H, —CH$_2$$\underline{H}_3$, J=6.0 Hz).

EXAMPLE 2

1-[(1E)-5-methoxycarbonylpent-1-enyl]-3-(1-hydroxynon-3-ynyl)benzene

The compound is obtained in accordance with the method of operation described in Example 1 with isolation of the E isomer by chromatography on a silica column.

EXAMPLE 3

1-[(1Z)-5-hydroxycarbonylpent-1-enyl]-3-(1-hydroxynon-3-ynyl)benzene 880 mg (2.57 mmols) of the compound of Example 1 are brought into solution in 30 ml of tetrahydrofuran to which 30 ml of an aqueous lithium hydroxide solution (2M) are added. The mixture is stirred vigorously at room temperature for 15 h and then acidified with 5 ml of acetic acid; the reaction mixture is then extracted with ether (3 times), the organic phases are treated in customary manner, and the acid obtained is purified by chromatography on a silica column (eluent: ether/petroleum ether 50:50 then 70:30). 730 mg of the expected hydroxy-acid are obtained in the form of a colourless oil which slowly crystallises.

Yield: 86% Melting point: 44° C.

EXAMPLE 4

Sodium Salt of the Acid of Example 3

728 mg (2.21 mmols) of the acid of Example 3 dissolved in methanol are added to 88.6 mg (2.21 mmols) of sodium hydroxide. The flask is shaken by hand until the sodium hydroxide has dissolved completely, and the methanol is then evaporated off in vacuo and the white precipitate obtained is washed with hexane and then dried. The expected sodium salt is obtained quantitatively in the form of a white powder.

Melting point: 130°–135° C.

EXAMPLE 5

1-[(1Z)-5-methoxycarbonylpent-1-enyl]-3-[(3Z)-1-hydroxynon-3-enyl]benzene

Step 5a: Catalytic hydrogenation of the compound obtained in Step 1c 4.5 g (9.32 mmols) of the aldehyde obtained in Step 1c are dissolved in 100 ml of n-hexane; 1 g of Lindlar catalyst and then 5 ml of pyridine are added. The mixture is stirred at room temperature under a hydrogen atmosphere for 1 hour 20 minutes, then filtered, and the filtrate is washed with a dilute hydrochloric acid solution and then dried (magnesium sulfate); the solvents are then evaporated off in vacuo and the crude product is purified by chromatography on a silica column (eluent: ether/petroleum ether, 10:90 then 20:80). 4.4 g of aldehyde in the form of a colourless oil are obtained.

Yield: 97%.

Step 5b:
1-[(1Z)-5-methoxycarbonylpent-1-enyl]-3-[(3Z)-1-hydroxynon-3-enyl]benzene This product is prepared in accordance with a method of operation identical to that described for the ester of Step 1d. Starting from 4.2 g of the aldehyde obtained in Step 5a, 4.4 g of a mixture of two isomers Z and E (Z/E: 90/10) are obtained, which are separated by chromatography on a silica column (eluent: ether/petroleum ether, 5:95). The Z isomer is subjected to a reaction for the deprotection of the alcohol function to obtain the expected hydroxy-ester in the form of a colourless oil.

Yield: 77%

Proton NMR spectrum characteristics (90 MHz, CDCl$_3$, δ ppm):

7.37–7.07 (m, 4H aromatic); 6.45 (d, 1H, ArC$\underline{H}$=CH—, J=11.6 Hz); 5.77–5.22 (m, 3H, ArCH=C$\underline{H}$—; —CH$_2$C$\underline{H}$=C$\underline{H}$CH$_2$—); 4.66 (t, 1H, HOC$\underline{H}$CH$_2$—, J=6.7 Hz); 3.61 (s, 3H, —CO$_2$C$\underline{H}_3$); 2.62–2.24 (7H: m, 4H, —C$\underline{H}_2$CH=CHC$\underline{H}_2$—; t, 2H, —C$\underline{H}_2$CO$_2$CH$_3$, J=6.7 Hz; and $\underline{H}$OCH—); 2.13–1.61 (m, 4H, —C$\underline{H}_2$C$\underline{H}_2$CH$_2$CO$_2$CH$_3$); 1.40–1.09 [m, 6H, —CH$_2$(C$\underline{H}_2$)$_3$]; 0.87 (t, 3H, —CH$_2$C$\underline{H}_3$, J=6.3 Hz).

EXAMPLE 6

1-[(1E)-5-methoxycarbonylpent-1-enyl]-3-[(3Z)-1-hydroxynon-3-enyl]benzene

This compound is obtained in a manner identical to that of the compound of Example 5, after isolation of the E isomer from Step 5b.

EXAMPLE 7

1-[(1Z)-5-hydroxycarbonylpent-1-enyl]-3-[(3Z)-1-hydroxynon-3-enyl]benzene

The process is the same as that described for the compound of Example 3.

Proton NMR spectrum characteristics (90 MHz, CDCl$_3$, δppm):

7.41–7.04 (m, 4H aromatic); 6.47 (d, 1H, ArCH̲=CH—, J=11.6 Hz); 5.96 (broad, 1H, —CO$_2$H̲); 5.80–5.21 (m, 3H, ArCH=CH̲—; —CH$_2$CH̲=CH̲CH$_2$—); 4.68 (t, 1H, HOCH̲CH$_2$—, J=6.7 Hz); 2.60–2.23 (m, 6H, —CH̲CO$_2$H; —CH̲$_2$CH=CHCH̲$_2$—); 2.05–1.67 (m, 5H, —CH̲$_2$CH̲$_2$CH$_2$CO$_2$H, HOCH—); 1.43–1.09 [m, 6H, —CH$_2$(CH̲$_2$)$_3$CH$_3$]; 0.87 (t, 3H, —CH$_2$CH̲$_3$, J=5.7 Hz).

EXAMPLE 8

Sodium Salt of Example 7

The process is identical to that described in Example 4, starting from the acid obtained in Example 7.
Proton NMR spectrum characteristics (90 MHz, D$_2$O, δppm):
7.50–7.28 (m, 4H aromatic); 6.59 (d, 1H, ArCH̲=CH—, J=11.2 Hz); 5.92 (dt, 1H, ArCH=CH̲CH$_2$, J=11.2; 7.3 Hz); 5.66–5.33 (m, 2H, —CH$_2$CH̲=CH̲CH$_2$—); 4.86 (t, 1H, HOCH̲— J=6.7 Hz); 2.86–2.29 (m, 6H, —CH̲$_2$CO$_2$$^-$Na$^+$; CH̲$_2$CH=CHCH̲$_2$—); 2.14–1.78 (m, 4H, —CH̲$_2$CH̲$_2$CH$_2$CO$_2$$^-$Na$^+$); 1.48–1.03 [m, 6H, —CH$_2$(CH̲$_2$)$_3$CH$_3$]; 0.88 (t, 3H, —CH$_2$CH̲$_3$, J=5.8 Hz).

EXAMPLE 9

Methyl (5Z)-6-[3-(1-hydroxyhexyl)phenyl]hex-5-enoate

Step 9a:
1-dimethoxymethyl-3-(1-hydroxyhexyl)benzene 54 ml of anhydrous tetrahydrofuran and an iodine crystal are added to 1.84 g (8.64 mmols) of metallic magnesium which has been flame-dried and then cooled under nitrogen. The mixture is refluxed, the yellow colour of the iodine disappears, and 11 ml (86.4 mmols) of 1-bromopentane dissolved in 50 ml of anhydrous tetrahydrofuran are added. After the addition, heating is continued for approximately 20 minutes (almost total consumption of the magnesium), the mixture is cooled under nitrogen at room temperature. Under nitrogen and with magnetic stirring, the magnesium solution prepared above is slowly added to a solution, cooled to −50° C., of 8.9 g (49.4 mmols) of acetal-aldehyde (Preparation B) in 90 ml of anhydrous tetrahydrofuran; the mixture, returned to room temperature, is hydrolysed with a saturated aqueous ammonium chloride solution and then extracted with ether (3 times). Treatment of the organic phases yields, after purification by chromatography on a silica column (eluent: ether/petroleum ether, 50:50 with 1% triethylamine), 9.8 g of the expected alcohol in the form of a colourless oil.
Yield: 78%.

Step 9b: Protection of the alcohol function

The process is the same as that described in Step 1b. Starting from 6.1 g of the alcohol obtained in Step 9a, after chromatography 9.7 g of silylated ether are isolated in the form of a colourless oil.
Yield: 82%.

Step 9c: Deprotection of the acetal function

The method of operation is identical to that described in Step 1c. Starting from 9.7 g of the acetal obtained in Step 9b, 8.4 g of aldehyde are obtained in the form of a colourless oil.
Yield: 96%.

Step 9d: Methyl (5Z)-6-[3-(1-hydroxyhexyl)phenyl]hex-5-enoate

The method of operation is identical to that described in Step 1d. Starting from 1.6 g of the compound obtained in Step 9c, after chromatography 700 mg of the Z configuration hydroxyester are isolated.
Yield: 80%
Proton NMR spectrum characteristics (90 MHz, CDCl$_3$, δppm):
7.47–7.07 (m, 4H aromatic); 6.46 (d, 1H, ArCH̲=CH—, J=11.4 Hz); 5.63 (dt, 1H, ArCH=CH̲CH$_2$—, J=11.4; 7.3 Hz); 4.66 (t, 1H, HOCH̲CH$_2$—, J=6.7 Hz); 3.64 (s, 3H, —CO$_2$CH̲$_3$); 2.49–2.20 [4H: 2H (t), —CH̲$_2$CO$_2$CH$_3$, J=6.8 Hz and 2H (m), —CH=CHCH̲$_2$—]; 2.13–1.57 (m, 5H, HOCH̲CH$_2$—, —CH̲$_2$CH$_2$CO$_2$CH$_3$); 1.42–1.15 [m, 6H, —CH$_2$(CH̲$_2$)$_3$CH$_3$]; 0.87 (t, 3H, —CH$_2$CH̲$_3$, J=6.0 Hz).

EXAMPLE 10

Methyl (5E)-6-[3-(1-hydroxyhexyl)phenyl]hex-5-enoate

This compound is obtained in accordance with the method of operation described in Example 9 with isolation of the E isomer by chromatography on a silica column.

EXAMPLE 11

1-[(1Z)-5-hydroxycarbonylpent-1-enyl]-3-(1-hydroxyhexyl)benzene

The method of operation is identical to that described in Example 3.
Yield: 86%
Proton NMR spectrum characteristics (90 MHz, CDCl$_3$, δppm):
7.44–7.02 (m, 4H aromatic); 6.47 (d, 1H, ArCH̲=CH—, J=11.4 Hz); 6.24 (s broadened, 2H, —CO$_2$H; —OH̲); 5.63 (dt, 1H, ArCH=CH̲—, J=11.4; 7.4 Hz); 4.64 (t, 1H, HOCH̲CH$_2$—, J=6.9 Hz); 2.59–2.17 (m, 4H, —CH̲$_2$CH$_2$CH$_2$CO$_2$H); 2.03–1.56 (m, 4H, HOCHCH̲$_2$—, —CH̲$_2$CH2CO$_2$H); 1.10–0.68 [m, 6H, —CH$_2$(CH̲$_2$)$_3$CH$_3$]; 0.86 (t, 3H, —CH$_2$CH̲$_3$, J=6.0 Hz).

EXAMPLE 12

Sodium (5Z)-6-[3-(1-hydroxyhex-1-yl)phenyl]hex-5-enoate

This salt is obtained quantitatively starting from the acid obtained in Example 11 and in accordance with a method of operation identical to that described in Example 4. The salt obtained is a white power.
Melting point: 140° C.

EXAMPLE 13

Methyl 6-[3-(1-hydroxyhexyl)phenyl]hexanoate 3.1 g (5.7 mmols) of the ester obtained in Example 10, the alcohol function of which is protected, are dissolved in 100 ml of ethyl acetate, and then 300 mg of palladium-on-carbon are added. The flask is then fitted with a catalytic hydrogenation apparatus and the mixture is stirred under a hydrogen atmosphere for 1 hour, then filtered. The solvent is subsequently evaporated off in vacuo and the crude product is purified by chromatography (eluent: ether/petroleum ether, 10:90). 3.1 g of ester are obtained, then the alcohol function is deprotected in accordance with the method described in Step 1d. The expected hydroxy-ester is in the form of a colourless oil.

Yield: 90%

Proton NMR spectrum characteristics (90 MHz, CDCl$_3$, δppm):

7.32–6.91 (m, 4H aromatic); 4.62 (t, 1H, HOCHCH$_2$—, J=6.7 Hz); 3.64 s, 3H, —CO$_2$CH$_3$); 2.61 (t, 2H, ARCH$_2$—, J=7.0 Hz); 2.29 (t, 2H, —CH$_2$CO$_2$CH$_3$, J=7.0 Hz); 2.11 (s broad, 1H, HOCH—). 1.95–1.06 (m, 14H, HOCH(CH$_2$)$_4$CH$_3$; —CH$_2$(CH$_2$)$_3$CH$_2$CO$_2$CH$_3$]; 0.87 (t, 3H, —CH$_2$CH$_3$, J=6.7 Hz).

EXAMPLE 14

1-(5-hydroxycarbonylpentyl)-3-(1-hydroxyhexyl)-benzene

The method of operation is identical to that described in Example 3. Starting from 1.3 g of the hydroxy-ester obtained in Example 13, after chromatography on a silica column 1.07 g of hydroxy-acid in the form of a colourless oil are isolated.

Yield: 87%

Proton NMR spectrum characteristics (90 MHz, (CD$_3$)$_2$CO, δ ppm):

7.55–6.90 (m, 4H aromatic); 4.61 (t, 1H, HOCHCH$_2$—, J=6.6 Hz); 2.61 (t, 2H, ArCH$_2$CH$_2$—, J=7.0 Hz); 2.28 (t, 2H, —CH$_2$CO$_2$H, J=7.0 Hz); 1.91–1.07 [m, 14H, HOCH(CH$_2$)$_4$CH$_3$; —CH$_2$(CH$_2$)$_3$CH$_2$CO$_2$H]; 0.86 (t, 3H, —CH$_2$CH$_3$, J=7.0 Hz).

EXAMPLE 15

Sodium 6-[3-(1-hydroxyhexyl)phenyl]hexanoate

The method of operation is identical to that described in Example 4. Starting from 1.7 g of the hydroxy-acid of Example 14, after washing 1.1 g of the expected salt are obtained in the form of a white powder.

Yield: 95% Melting point: 165° C.

EXAMPLE 16

2-[(1Z)-5-methoxycarbonylpent-1-enyl]-6-(1-hydroxyhexyl)pyridine

Step 16a:
2-hydroxymethyl-6-(tert-butyldiphenylsilyloxymethyl)-pyridine 2.87 g (72 mmols) of 60% sodium hydride in mineral oil are washed with petroleum ether (3 times) and then suspended in 150 ml of anhydrous tetrahydrofuran for the addition of 10 g (72 mmols) of 2,6-dimethanolpyridine. The mixture is then stirred at 50° C. for 6 hours (a white precipitate, the mono-alcoholate, appears in suspension), then 18.5 ml (72 mmols) of tert-butyldiphenylsilyl chloride are added dropwise, at room temperature, and the solution is stirred for 2 hours. After hydrolysis, the reaction mixture is extracted with ether (3 times), the organic phases are treated in customary manner, and the oily residue is chromatographed on a silica column (eluent: ether/petroleum ether, 50:50). 16.5 g of the expected product are obtained in the form of a colourless oil.

Yield: 61%

Step 16b:
2-formyl-6-(tert-butyldiphenylsilylmethyl)pyridine 4.3 ml (48 mmols) of oxalyl chloride dissolved in 6 ml of dichloromethane are cooled to –60° C. for the dropwise addition, under nitrogen and with magnetic stirring, of a solution of 7.6 ml of dimethyl sulfoxide in 24 ml of dichloromethane. After 20 minutes' stirring at –60° C., 16 g (44 mmols) of the compound obtained in Step 16a in 60 ml of dichloromethane are added dropwise. The whole is stirred at –60° C. for 30 min. and then 32 ml of triethylamine are slowly added. The reaction mixture is stirred until it has returned to room temperature, and is then hydrolysed and extracted with ether (3 times). After treatment of the organic phase and purification on a silica column (eluent: ether/petroleum ether, 20:80), 14.5 g of the expected aldehyde are obtained.

Yield: 91%

Step 16c:
2-[(1Z)-5-methoxycarbonylpent-1-enyl]-6-(1-hydroxyhexyl)pyridine

The method of operation is identical to that described in Step 1d of Example 1.

Yield: 76% Melting point: 38°–40° C.

Step 16d: 2-[(1Z)-5-methoxycarbonylpent-1-enyl]-6-formylpyridine

The method of operation is identical to that described in Step 16b.

Yield: 98%

Step 16e:
2-[(1Z)-5-methoxycarbonylpent-1-enyl]-6-(1-hydroxyhexyl)pyridine

A solution of n-hexylmagnesium bromide in tetrahydrofuran (freshly prepared from 486 mg (20 mmols) of metallic magnesium and 2.5 ml (20 mmols) of n-hexyl bromide) are added to a solution, cooled to –60° C., of 3 g (12.8 mmols) of the aldehyde obtained in Step 16d in 24 ml of anhydrous toluene. After stirring for 1 hour at reduced temperature and then returning to room temperature, the mixture is hydrolysed with a saturated aqueous ammonium chloride solution and then extracted with ether (3 times). The organic phases are treated in customary manner and the oily residue is chromatographed on a silica column (eluent: ether/petroleum ether, 50:50) to yield 1.8 g of the expected hydroxy-ester in the form of a colourless oil.

Yield: 76%

Proton NMR spectrum characteristics (90 MHz, CDCl$_3$, δ ppm):

7.63 (t, 1H aromatic, H$_4$, J=7.7 Hz); 7.12–7.01 (dd, 2H, H$_3$ and H$_5$, J=7.7; 2.5 Hz); 6.45 (dt, 1H, ArCH=CH—, J=11.7; 1.5 Hz); 5.85 (dt, 1H, ArCH=CHCH$_2$—, J=11.7; 7.2 Hz); 4.73 (t, 1H, HOCHCH$_2$—, J=6.7 Hz); 4.40 (broad, 1H, HOCH—); 3.65 (s, 3H, —CO$_2$CH$_3$); 2.71 (q, 2H, ArCH=CHCH$_2$—, J=7.2 Hz); 2.38 (t, 2H, —CH$_2$CO$_2$CH$_3$, J=7.3 Hz); 1.83 (p, 4H, —CH$_2$CH$_2$CO$_2$CH$_3$, J=7.0; HOCHCH$_2$-masked by the pentuplet); 1.56–1.16 [m, 6H, —CH$_2$(CH$_2$)$_3$CH$_3$]; 0.87 (t, 3H, —CH$_2$CH$_3$, J=6.8 Hz).

EXAMPLE 17

2-[(1Z)-5-hydroxy carbonylpent-1-enyl]-6-(1-hydroxyhexyl)pyridine

The method of operation is identical to that described for the compound of Example 3.

Yield: 87%

Proton NMR spectrum characteristics (90 MHz, CDCl$_3$, δppm):

7.63 (t, 1H aromatic, H4, J=7.7 Hz); 7.32–6.95 (m, 3H, 2H aromatic, —CO$_2$H); 6.46 (d, 1H, ArCH=CH—, J=11.6 Hz); 5.86 (dt, 1H, ArCH=CHCH$_2$—, J=11.7; 7.2 Hz); 4.73 (t, 1H, HOCHCH$_2$—, J=5.8 Hz); 2.70 (pseudo q, 2H, —CH=CHCH$_2$—, J=7.5 Hz); 2.40 (t, 2H, —CH$_2$CO$_2$H, J=7.2 Hz); 2.00–1.56 (m, 4H, —CH$_2$CH$_2$CO$_2$H; HOCHCH$_2$—); 1.50–1.03 [m, 7H, —CH$_2$(CH$_2$)$_3$CH$_3$; HOCH—]; 0.86 (t, 3H, —CH$_2$CH$_3$, J=5.8 Hz).

EXAMPLE 18

Sodium (5Z)-6-[6-(1-hydroxyhex-1-yl)pyrid-2-yl]hex-5-enoate

The method of operation is identical to that described in Example 4. The compound is obtained starting from the compound of Example 17.

Quantitative yield Melting point: 130° C.

EXAMPLE 19

(5Z)-N-methyl-6-[3-(1-hydroxyhexyl)phenyl]hex-5-en-1-hydroxamic acid

44 μl (≈0.6 mmols) of N,N-dimethylformamide are added, under nitrogen, to 320 mg (0.6 mmols) of the acid obtained in Example 11, the alcohol function of which has been protected beforehand by diphenyl-tert-butylsilyl chloride, dissolved in 5 ml of anhydrous tetrahydrofuran. The mixture is cooled to 0° C. for the addition of 105 μl (1.2 mmols, 2 equivalents) of oxalyl chloride. Stirring is maintained at 0° C. under nitrogen for 1 hour 30 minutes to yield the corresponding acyl chloride. 600 μl (1.8 mmols) of a 3N sodium hydroxide solution are added to 75 mg (0.9 mmols) of N-methylhydroxylamine hydrochloride in 2 ml of water. The mixture is stirred for 30 minutes and then cooled to 0° C. for the rapid addition, using a syringe, of the crude acyl chloride solution formed above. After two hours' stirring, the reaction mixture is extracted with ether (3 times), the organic phases are washed and then dried (magnesium sulfate), the solvents are evaporated off in vacuo, and the crude product obtained is subjected to a reaction for the deprotection of the alcohol function and then purified by chromatography on a silica column (eluent: ether/petroleum ether, 20:80; 50:50, then ether only). 90 mg of the hydroxamic acid of the title are obtained in the form of a colourless oil.

Yield: 47%

Proton NMR spectrum characteristics (90 MHz, CDCl$_3$, δ ppm):

7.41–6.99 (m, 4H aromatic); 6.43 (d, 1H, ArCH=CH—, J=11.3 Hz); 5.62 (dt, 1H, ArCH=CHCH$_2$—, J=11.4; 7.2 Hz); 4.60 (t, 1H, HOCHCH$_2$—, J=6.2 Hz); 3.30–2.98 (m, 3H, —N(OH)—CH$_3$); 2.54–2.08 (m, 4H, —CH$_2$CH$_2$CH$_2$CON); 1.95–1.52 (m, 4H, —CH$_2$CH$_2$CON; HOCHCH$_2$—); 1.44–1.10 [m, 6H, —CH$_2$(CH$_2$)$_3$CH$_3$]; 0.86 (t, —3H, CH$_2$CH$_3$, J=6.2 Hz).

EXAMPLE 20

(1Z)-6-[3-(1-hydroxyhexyl)phenyl]hex-5-en-1-ol 7 ml (7 mmols) of a 1M diisobutylaluminium hydride solution in toluene are added dropwise, under nitrogen and with magnetic stirring, to a solution, cooled to −40° C., of 1.80 g (3.31 mmols) of the ester obtained in Example 9, the alcohol function of which has been protected beforehand by diphenyl-tert-butylsilyl chloride, in 65 ml of anhydrous ether. 10 minutes after the end of the addition, the reaction mixture is hydrolysed with water, and a white gelatinous precipitate forms which is dissolved by the addition of a saturated aqueous potassium sodium tartrate solution. The mixture is extracted with ether (3 times), the organic phases are dried (magnesium sulfate) and then filtered, the solvents are subsequently evaporated in vacuo and the residue obtained is subjected to a reaction for the deprotection of the alcohol function and then chromatographed on a silica column (eluent: ether/petroleum ether, 50:50). The alcohol of the title is obtained in the form of a colourless oil.

Yield: 70%

Proton NMR spectrum characteristics (90 MHz, CDCl$_3$, δ ppm):

7.39–7.01 (m, 4H aromatic); 6.43 (dt, 1H, ArCH=CH—, J=11.4; 1.6 Hz); 5.66 (dt, 1H, ArCH=CH—, J=11.4; 7.3 Hz); 4.64 (t, 1H, HOCHCH$_2$—, J=6.2 Hz); 3.60 (t, 2H, —CH$_2$OH, J=6.8 Hz); 2.50–2.12 (q broadened, 2H, —CH=CHCH$_2$—); 1.90–1.08 [m, 14H, —CH$_2$CH$_2$CH$_2$OH; HOCH(CH$_2$)$_4$CH$_3$]; 0.87 (t, 3H, —CH$_2$CH$_3$, J=6.0 Hz).

EXAMPLE 21

1-[6-(1Z)-bromohex-1-en-1-yl]-3-(1-hydroxyhexyl)-benzene

Step 21a:
1-[6-(1Z)-bromohex-1-en-1-yl]-3-[1-(diphenyl-tert-butylsilyloxy)hexyl]benzene A solution of 714 mg (2.7 mmols) of triphenylphosphine in 8 ml of dichloromethane is added dropwise, under nitrogen and with magnetic stirring, to a solution, cooled to 0° C., of 1.0 g (2.0 mmols) of the alcohol obtained in Example 20, isolated before the secondary alcohol is freed, and 840 mg (2.5 mmols) of tetrabromomethane in 16 ml of dichloromethane. After 15 minutes' stirring at 0° C., the petroleum ether is added cold and the reaction mixture is filtered over silica, the solvents are evaporated off in vacuo, and the oil obtained is purified by flash chromatography (eluent: ether/petroleum ether, 5:95). 1.15 g of the brominated title compound are obtained in quantitative yield in the form of a colourless oil.

Proton NMR spectrum characteristics (90 MHz, CDCl$_3$, δ ppm):

7.78–7.58 (m, 2H aromatic); 7.54–6.97 (m, 12H aromatic); 6.40 (dt, 1H ArCH=CH—, J=11.5; 1.6 Hz); 5.58 (dt, 1H, —CH=CHCH$_2$—, J=11.6; 7.2 Hz); 4.64 (t, 1H, SiOCHCH$_2$—; J=6.0 Hz); 3.33 (t, 2H, —CH$_2$Br, J=6.5 Hz); 2.35 (q broadened, 2H, CH=CHCH$_2$—, J=7.2 Hz); 2.00–1.45 (m, 6H, SiOCHCH$_2$—; —CH$_2$CH$_2$CH$_2$Br); 1.19–0.94 [m, 15H, —CH$_2$(CH$_2$)$_3$CH$_3$, —C(CH$_3$)$_3$]; 0.76 (t, 3H, —CH$_2$CH$_3$, J=6.0 Hz).

Step 21 b: 1-[6-(1Z)-bromohex-1-en- 1-yl]-3-(1-hydroxyhexyl)benzene

The bromide obtained in the preceding Step is treated with tetra-n-butylammonium fluoride in order to free the alcohol function.

EXAMPLE 22

1-[(1Z)-6-diethoxyphosphinylhex-1-enyl]-3-(1-hydroxyhexyl)benzene 420 mg (0.72 mmols) of the brominated compound obtained in Step 21a are added to 7 ml of triethyl phosphite. The mixture is heated to 130°–140° under nitrogen and with magnetic stirring for 7 hours, then the excess triethyl phosphite is distilled off in vacuo. The crude product is subjected to a reaction to free the secondary alcohol function, then purified by chromatography on a silica column (eluent: ether). 235 mg of the expected phosphonate are obtained in the form of a colourless oil.

Yield: 82%
Proton NMR spectrum characteristics (90 MHz, CDCl$_3$, δ ppm):
7.40–7.06 (m, 4H aromatic); 6.44 (dt, 1H, ArC$\underline{H}$=CH—, J=11.4; 1.3 Hz); 5.62 (dt, 1H, ArCH=C$\underline{H}$—, J=11.4; 7.3 Hz); 4.63 (t, 1H, HOC$\underline{H}$CH$_2$—, J=6.2 Hz); 4.04 [p, 4H, —PO(OC$\underline{H}_2$CH$_3$)$_2$, J=7.2 Hz); 2.70 (broad, 1H, $\underline{H}$OCH—); 2.33 (q broadened, 2H, —CH=CHC$\underline{H}_2$—); 1.74–1.53 [m, 8H, —CH$_2$(C$\underline{H}_2$)$_3$PO(OEt)$_2$; HOCHC$\underline{H}_2$—]; 1.28 [t, 12H, —PO(OCH$_2$C$\underline{H}_3$)$_2$, J=7.2 Hz; —CH$_2$(C$\underline{H}_2$)$_3$CH$_3$ masked by the triplet); 0.87 (t, 3H, —CH$_2$C$\underline{H}_3$, J=6.3 Hz).

EXAMPLE 23

1-[(1Z)-6-aminohex-1-enyl]-3-(1-hydroxyhexyl)benzene

Step 23a:
1-[(1Z)-6-azidohex-1-enyl]-3-[1-(diphenyl-tert-butylsilyloxy)hexyl]benzene 107 mg (1.6 mmols) of sodium azide (NaN$_3$) are added to a solution of 590 mg (1.02 mmols) of the brominated compound obtained in Step 21a in 10 ml of dimethyl sulfoxide. The mixture is stirred at room temperature, under nitrogen, for 3 hours, then water is added and the reaction mixture is extracted with ether (3 times). The organic phases are washed with water, then dried (magnesium sulfate) and filtered, the solvents are then evaporated off in vacuo and the crude product is purified by flash chromatography (eluent: ether/petroleum ether, 5:95). 530 mg of the expected azide are obtained in the form of a colourless oil.

Yield: 96%.
Proton NMR spectrum characteristics (90 MHz, CDCl$_3$, δ ppm):
7.75–7.62 (m, 2H aromatic); 7.55–6.95 (m, 12H, aromatic); 6.40 (d, 1H, ArC$\underline{H}$=CH—, J=11.6 Hz); 5.58 (dt, 1H, ArCH=C$\underline{H}$CH$_2$—, J=11.3; 7.0 Hz); 4.63 (t, 1H, SiOC$\underline{H}$CH$_2$—, J=5.9 Hz) 3.20 (t, 2H, —C$\underline{H}_2$N$_3$, J=6.3 Hz); 2.31 (q broadened, 2H, —CH=CHC$\underline{H}_2$); 1.76–1.38 [m, 6H, —CH$_2$(C$\underline{H}_2$)$_2$CH$_2$N$_3$, SiOCHC$\underline{H}_2$—]; 1.19–0.90 [m, 15H, —CH$_2$(C$\underline{H}_2$)$_3$CH$_3$; —C(C$\underline{H}_3$)$_3$]; 0.75 (t, 3H, —CH$_2$C$\underline{H}_3$, J=6.0 Hz).

Step 23b:
1-[(1Z)-6-azidohex-1-enyl]-3-(1-hydroxyhexyl)benzene 500 mg of the azide obtained in the preceding Step are subjected to a reaction for the deprotection of the alcohol function. After chromatography, 250 mg of the expected azide are obtained in the form of a colourless oil.

Yield: 89%

Step 23c:
1-[(1Z)-6-aminohex-1-enyl]-3-(1-hydroxyhexyl)benzene 140 mg (0.53 mmols) of triphenylphosphine and then 14 μl of water and a pumice stone are added to a solution of 160 mg (0.53 mmols) of the azide obtained in the preceding Step in 0.5 ml of tetrahydrofuran (an evolution of nitrogen is observed). The mixture is left at room temperature for 8 hours, then the tetrahydrofuran is evaporated off in vacuo and the residue is chromatographed on a silica column using methanol as eluent. 100 mg of the expected amine are obtained in the form of a colourless oil.

Yield: 68%
Proton NMR spectrum characteristics (90 MHz, CDCl$_3$, δ ppm):
7.37–7.05 (m, 4H aromatic); 6.41 (d, 1H, ArC$\underline{H}$=CH—, J=11.6 Hz); 5.62 (dt, 1H, ArCH=C$\underline{H}$CH$_2$—, J=11.6; 7.2 Hz); 4.49 (t, 1H, HOC$\underline{H}$CH$_2$—, J=6.3 Hz); 2.72–2.45 (m, 2H, —C$\underline{H}_2$NH$_2$); 2.45–2.08 (m, 5H of which 3 are exchangeable with D$_2$O, —CH=CHC$\underline{H}_2$—; $\underline{H}$OCH—; $\underline{H}_2$NCH$_2$—); 1.83–1.55 (m, 2H, HOCHC$\underline{H}_2$—); 1.55–1.10 [m, 10H, —CH$_2$(C$\underline{H}_2$)$_3$CH$_3$; —CH(C$\underline{H}_2$)$_2$CH$_2$NH$_2$]; 0.86 (t, 3H, —CH$_2$C$\underline{H}_3$, J=6.1 Hz).

EXAMPLE 24

1-[(1Z)-6-(p-toluenesulfonylamino)hex-1-enyl]-3-(1-hydroxyhexyl)benzene

120 μl (0.84 mmols) of anhydrous triethylamine, then 120 mg (0.62 mmols) of p-toluenesulfonyl chloride, are added under nitrogen and with magnetic stirring to 200 mg (0.39 mmols) of the amine obtained in Example 23 in 1 ml of dichloromethane, which amine has been cooled to 0° C. and the alcohol function of which has been protected beforehand by diphenyl-tert-butylsilyl chloride. After 15 minutes' stirring at 0° C., water is added, the reaction mixture is then extracted with ether (3 times), and the organic phases are washed with a saturated sodium chloride solution and then dried (magnesium sulfate) and filtered. The solvents are then evaporated off in vacuo and the oil obtained is subjected to a reaction for the deprotection of the alcohol function and then purified by chromatography on a silica column (eluent: ether/petroleum ether, 50:50). 120 mg of the expected sulfamide are obtained in the form of a colourless oil.

Yield: 72%
Proton NMR spectrum characteristics (90 MHz, CDCl$_3$, δ ppm):
7.70 (dt, 2H aromatic at the position α to —SO$_2$NH—, J=8.3; 1.3 Hz); 7.40–7.05 (m, 6H aromatic); 6.39 (d, 1H, ArC$\underline{H}$=CH—, J=11.8 Hz); 5.54 (dt, 1H, ArCH=C$\underline{H}$—, J=11.8; 7.4 Hz); 5.10 (t, 1H exchangeable with D$_2$O, —N$\underline{H}$SO$_2$—; J=6.2 Hz); 4.63 (t, 1H, HOC$\underline{H}$CH$_2$—, J=6.3 Hz); 2.83 (q broadened, 2H, —C$\underline{H}_2$NH—); 2.50 (s, 1H exchangeable with D$_2$O, $\underline{H}$OCH—); 2.39 (s, 3H, p—C$\underline{H}_3$C$_6$H$_4$—); 2.24 (q broadened, 2H, —CH=CHC$\underline{H}_2$—); 1.85–1.58 (m, 2H, HOCHC$\underline{H}_2$—); 1.50–1.18 [m, 10H, —CH$_2$(C$\underline{H}_2$)$_3$CH$_3$; —CH$_2$(C$\underline{H}_2$)$_2$CH$_2$NH—]; 0.85 (t, 3H, —CH$_2$C$\underline{H}_3$, J=6.0 Hz).

EXAMPLE 25

(5Z)-6-[3-(1-hydroxyhexyl)phenyl]hex-5-en-1-al oxime

The alcohol obtained in Example 20, the secondary alcohol function of which has been protected beforehand by diphenyl-tert-butylsilyl chloride, is oxidised by pyridinium chlorochromate in the presence of sodium acetate in methylene chloride. The aldehyde so-obtained is treated with hydroxylamine hydrochloride to yield the expected product in racemic form after deprotection of the alcohol function.
Proton NMR Spectrum characteristics (90 MHz, CDCl$_3$, δ ppm):
7.55–7.07 (m, 5H arom+C$\underline{H}$=N); 6.45 (d, 1H, J=11.4); 5.63 (dt, 1H, J=11.4, J=7.3); 4.65 (t, 1H, J=6.6); 2.76–2.05 (m, 4H); 2.05–1.00 (m, 11H); 1.00–0.71 (m, 3H)

EXAMPLE 26

Sodium (5Z)-6-{3-[(3Z)-(1-hydroxynon-3-en-1-yl)]-phenyl}hex-5-enoate

This compound is prepared starting from the acid described in Example 7 in accordance with the method described for obtaining the compound of Example 4.
Proton NMR spectrum characteristics (90 MHz, D$_2$O, δ ppm:
7.50–7.28 (m, 4H aromatic); 6.59 (d, 1H, ArC$\underline{H}$=CH—, J=11.2 Hz); 5.92 (dt, 1H, ArCH=C$\underline{H}$CH$_2$—, J=7.3; 11.2 Hz); 5.52 (unresolved peak, 2H; —CH$_2$C$\underline{H}$=CHCH$_2$—); 4.86 (t, 1H, HOC$\underline{H}$CH$_2$—, J=6.7 Hz); 2.86–2.29 (m, 6H, —C$\underline{H}_2$CO$_2^-$Na$_2^+$; —C$\underline{H}_2$CH=CHC$\underline{H}_2$—); 2.14–1.78 (unresolved peak, 4H, ArCH=CHC$\underline{H}_2$CH$_2$—); 1.22 (unresolved peak; 6H, —CH$_2$(C$\underline{H}_2$)$_3$CH$_3$); 0.88 (t, 3H, —CH$_2$C$\underline{H}_3$, J=5.8 Hz).

EXAMPLE 27

Methyl (5Z)-6-[3-(1-hydroxy-1-n-butylhexyl)phenyl]hex-5-enoate

Step 27a: Methyl (5Z)-6-[3-(1-oxohexyl)phenyl]hex-5-enoate

220 μl (2.5 mmols) of phosgene dissolved in 6 ml of dichloromethane are cooled to –60° for the dropwise addition, under nitrogen and with magnetic stirring, of a solution of 390 μl of dimethyl sulfoxide in 1.2 ml of dichloromethane. After 20 minutes' stirring at –60°, 680 mg (2.23 mmols) of the hydroxy-ester obtained in Example 9 dissolved in 3 ml of dichloromethane are added (dropwise). The solution is stirred (at –60°) for 30 minutes before the slow addition of 1.6 ml of triethylamine, and the whole is left to return to room temperature, with stirring, for a period of 30 minutes. The reaction mixture is then mixed with water and subsequently extracted with ether (3 times), and the organic phases are washed with water and then dried (magnesium sulfate) and filtered. The solvents are then evaporated off in vacuo and the crude product is purified by chromatography on a silica column (eluent: ether/petroleum ether, 20:80). 630 mg of the expected keto ester are obtained in the form of a colourless oil.
Yield: 93%

Step 27b: Methyl (5Z)-6-[3-(1-hydroxy-1-n-butylhexyl)phenyl]hex-5-enoate

The compound obtained in the preceding Step is placed in anhydrous tetrahydrofuran which has been cooled to –60° C. and then butyllithium is added. The title product is obtained after purification by chromatography on a silica column.

EXAMPLE 28

Methyl(5Z)-6-[(1R)-3-(1-hydroxyhexyl)phenyl]hex-5-enoate 5.5 ml (5.5 mmols) of a 1M boron hydride solution in tetrahydrofuran are added to 470 mg (1.85 mmols) of S-(–)-diphenylprolinol dissolved in 9 ml of anhydrous tetrahydrofuran. The whole is refluxed for two hours. After cooling, the solvent is removed in vacuo and the residue is dried, also in vacuo. The residue is taken up in 5 ml of anhydrous tetrahydrofuran and cooled to 0° C. 2 ml (2 mmols) of 1M boron hydride in tetrahydrofuran are added and then, after the whole has been stirred for a few minutes, 560 mg (1.85 mmols) of the compound obtained in Example 27, Step 27a are added. The reaction mixture is then neutralised by a few milliliters of methanol, the solvents are evaporated off in vacuo and the residue is taken up in ether. Customary treatment of the organic phase yields 370 mg of the expected compound after purification on a silica column (eluent: ether/petroleum ether, 50:50).
Yield: 66% Index of rotation: $[\alpha]_D^{20}$=+9.4 (concentration: 3.7×10$^{-3}$M in methanol)

EXAMPLE 29

(5Z)-6-[(1R)-3-(1-hydroxyhexyl)phenyl]hex-5-enoic acid

This compound is obtained in accordance with a method of operation analogous to that described in Example 3, starting from the ester obtained in Example 28.

EXAMPLE 30

Sodium(5Z)-6-[(1R)--3-(1-hydroxyhexyl)phenyl]hex-5-enoate

This compound is obtained in accordance with a method of operation analogous to that described in Example 4, starting from the acid obtained in Example 29.
Index of rotation: $[\alpha]_D^{20}$=+12.8 (concentration: 4.4×10$^{-3}$M in methanol)

Elemental microanalysis: C$_{18}$H$_{25}$O$_3$Na (molecular weight: 312.29)

|  | C | H |
|---|---|---|
| % calculated | 69.21 | 8.07 |
| % found | 69.49 | 8.09 |

EXAMPLE 31

Methyl(5Z)-6-[(1S)-3-(1-hydroxyhexyl)phenyl]hex-5-enoate

This compound is obtained in accordance with a method of operation analogous to that described in Example 28, replacing the S-(–)-diphenylprolinol with R-(+)-diphenylprolinol.
Yield: 63% Index of rotation: $[\alpha]_D^{20}$=–9.3 (concentration: 4.3×10$^{-3}$M in methanol)

EXAMPLE 32

(5Z)-6-[(1S)-3-(1-hydroxyhexyl)phenyl]hex-5-enoic acid

This compound is obtained in accordance with a method of operation analogous to that described in Example 3, starting from the ester obtained in Example 31.

EXAMPLE 33

Sodium (5Z)-6-[(1S)-3-(1-hydroxyhexyl)phenyl]hex-5-enoate

This compound is obtained in accordance with a method of operation analogous to that described in Example 4, starting from the acid obtained in Example 32.

Index of rotation: $[\alpha]_D^{20}=-12.9$ (concentration: $3.2\times10^{-3}$M in methanol)

Elemental microanalysis: $C_{18}H_{25}O_3Na$ (molecular weight: 312.29)

|  | C | H |
|---|---|---|
| % calculated | 69.21 | 8.07 |
| % found | 68.97 | 8.02 |

EXAMPLE 34

Methyl(5Z)-6-[3-(6-hydroxy-6-undecanyl)phenyl]hex-5-enoate

This compound is obtained in accordance with the method of operation described in Example 9, starting from the compound obtained in Example 27, Step 27a.

Yield: 64%

Proton NMR spectrum characteristics (90 MHz, $CDCl_3$, $\delta$ (ppm)):

7.41–7.01 (m, 4H aromatic); 6.48 (d, 1H, ArC$\underline{H}$=CH—, J=11.4 Hz); 5.62 (dt, 1H, ArCH=C$\underline{H}$—, J=11.9; 7.3 Hz); 3.63 (s, 3H, —$CO_2C\underline{H}_3$); 2.45–2.20 (4H: t, 2H, —C$\underline{H}_2CO_2CH_3$, J=7.0 Hz and 2H: —CH=CHC$\underline{H}_2$— masked by the triplet); 1.95–1.55 [m, 7H, —C$\underline{H}_2$CH$_2CO_2CH_3$; (—C$\underline{H}_2C_4H_9)_2$ and $\underline{H}$OC—]; 1.40–0.99 [m, 12H, HOC—(CH$_2$C$\underline{H}_2$CH$_2$CH$_3)_2$]; 0.82[pseudo triplet, 6H, (—CH$_2$C$\underline{H}_3)_2$].

EXAMPLE 35

Methyl(5Z)-6-{3-[hydroxy-(1Z)-(4-pent-1-enylphenyl)methyl]phenyl}hex-5-enoate

Step 35a: 1-(4-bromophenyl)pent-1-ene 52 ml (83.2 mmols) of a 1.6M n-butyllithium solution in hexane are added to a suspension, cooled to −10° C., of 34 g (85.1 mmols) of n-butyltriphenylphosphonium bromide in 150 ml of tetrahydrofuran. After 20 minutes' reaction, the whole is cooled to −80° C. and 50 ml of hexamethylphosphoric triamide are added, as well as 10 g (54 mmols) of 4-bromobenzaldehyde dissolved in 40 ml of tetrahydrofuran. After returning to room temperature and hydrolysis with a saturated ammonium chloride solution, the reaction mixture is extracted with ether. Customary treatment of the organic phase yields 10 g of the expected compound after purification by chromatography on a silica column (eluent: petroleum ether).

Yield: 82%

Step 35b: (3-dimethoxymethylphenyl)-(4-pent-1-enylphenyl)methanol 17 ml (23.8 mmols) of a 1.4M solution of sec-butyllithium in cyclohexane are added to a solution of 4.6 g (20.4 mmols) of the compound obtained in the preceding Step in 80 ml of tetrahydrofuran at −80° C. After 10 minutes' stirring, 3.7 g (20.5 mmols) of the compound obtained in Preparation B, in 15 ml of anhydrous tetrahydrofuran, are added. After returning to room temperature and hydrolysis with a saturated ammonium chloride solution, the reaction mixture is extracted with ether. Customary treatment of the organic phase yields 5.3 g of the expected compound after purification by chromatography on a silica column (eluent: ether/petroleum ether, 40:60 then 50:50 with 1% triethylamine).

Yield: 79%

Step 35c:

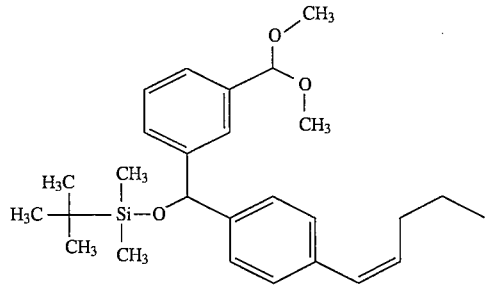

1.1 g (16.1 mmols) of imidazole, then 1.2 g (7.9 mmols) of dimethyl-tert-butylsilyl chloride, are added to a solution of 2.1 g (6.4 mmols) of the compound obtained in Step 35b in 25 ml of dimethylformamide. The mixture is left at room temperature for 15 hours and then hydrolysed with water. The reaction mixture is extracted with ether. Customary treatment of the organic phase yields 2.6 g of the expected silylated ether after purification on a silica column (eluent: ether/petroleum ether, 10:90 with 1% triethylamine).

Yield: 92%

Step 35d:

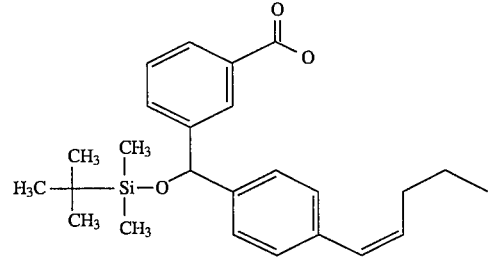

The compound is obtained in a quantitative yield in accordance with the method of operation described in Example 1, Step 1c, starting from the silylated ether obtained in the preceding Step.

Step 35e: Methyl (5Z)-6-{3-[hydroxy-(1Z)-(4-pent-1-enylphenyl)-methyl]phenyl}hex-5-enoate The compound is obtained in accordance with the method of operation described in Example 1, Step 1d, starting from the compound obtained in the preceding Step.

Yield: 81%

Proton NMR spectrum characteristics (300 MHz, CDCl$_3$, δ (ppm)):

7.38–7.12 (m, 8H aromatic); 6.44 (d, 1H, ArCH=CH—, J=11.6 Hz); 6.38 (dt, 1H, ArCH=CH—, J=11.7; 1.8 Hz); 5.84 (s, 1H, HOCH—); 5.66 (dt, 1H, —CH=CHCH$_2$—, J=11.7; 7.3 Hz); 5.63 (dt, 1H, —CH=CHCH$_2$—, J=11.5; 7.5 Hz); 3.62 (s, 3H, —CO$_2$CH$_3$); 2.5 (broad, 1H, HOCH—); 2.37–2.24 (m, 6H, —CH$_2$CH$_2$CH$_2$CO$_2$CH$_3$; Ar'CH=CHCH$_2$—); 1.75 (tt, 2H, —CH$_2$CH$_2$CO$_2$CH$_3$, J=7.5 Hz); 1.46 (tq, 2H, —CH$_2$CH$_3$, J=7.4 Hz); 0.92 (t, 3H, —CH$_2$CH$_3$, J=7.3 Hz).

Elemental microanalysis: C$_{25}$H$_{30}$O$_3$ (molecular weight: 378.52)

|  | C | H |
|---|---|---|
| % calculated | 79.33 | 7.99 |
| % found | 79.44 | 8.16 |

EXAMPLE 36

Methyl(5Z)-6-{3-[hydroxy-(4-pentylphenyl)methyl]-phenyl}hex-5-enoate 250 mg of palladium-on-carbon are added to 2.8 g (6.3 mmols) of the compound obtained in Example 35, Step 35c in 120 ml of ethyl acetate. The whole is maintained under a hydrogen atmosphere with stirring for 30 minutes. The hydrogenation product so obtained is subjected, after purification by chromatography, to the treatments described in Steps 35d and 35e in order to yield the expected product.

Total yield: 71%

Proton NMR spectrum characteristics (90 MHz, CDCl$_3$, δ (ppm)):

7.38–7.02 (m, 8H aromatic); 6.43 (d, 1H, CH=CHCH2—, J=11.3 Hz); 5.77 (d, 1H, HOCH—, J=2.9 Hz); 5.60 (dt, 1H, —CH=CHCH$_2$, J=11.6; 7.3 Hz); 3.60 (s, 3H, —CO$_2$CH$_3$); 2.73–2.14 (m, 7H, —CH$_2$CH$_2$CH$_2$CO$_2$CH$_3$; ArCH$_2$; HOCH—); 1.94–1.18 [m, 8H, —CH$_2$(CH$_2$)$_3$CH$_3$; —CH$_2$CH$_2$CO$_2$CH$_3$]; 0.88 (t, 3H, —CH$_2$CH$_3$, J=5.8 Hz).

Elemental microanalysis: C$_{25}$H$_{32}$O$_3$ (molecular weight: 380.53)

|  | C | H |
|---|---|---|
| % calculated | 78.91 | 8.48 |
| % found | 78.90 | 8.40 |

The acids described in the following Examples 37, 38 and 39 are obtained in accordance with the method of operation described in Example 29, starting from Examples 34, 35 and 36 respectively.

EXAMPLE 37

(5Z)-6-[3-(6-hydroxy-6-undecanyl)phenyl]hex-5-enoic acid

EXAMPLE 38

(5Z)-6-{3-[hydroxy-(1Z)-(4-pent-1-enylphenyl)-methyl]phenyl}hex-5-enoic acid

EXAMPLE 39

(5Z)-6-{3-[hydroxy-(4-pentylphenyl)methyl]-phenyl}hex-5-enoic acid

The sodium salts described in the following Examples 40, 41 and 42 are obtained in accordance with the method of operation described in Example 30, starting from Examples 37, 38 and 39 respectively.

EXAMPLE 40

Sodium (5Z)-6-[3-(6-hydroxy-6-undecanyl)phenyl]hex-5-enoate

Proton NMR spectrum characteristics (90 MHz, CD$_3$OD δ (ppm)):

7.40–7.03 (m, 4H aromatic); 6.44 (d, 1H, ArCH=CH—, J=12.2 Hz); 5.72 (dt, 1H, ArCH=CH—, J=12.2; 7.1 Hz); 2.42–2.14 (m, 4H, —CH$_2$CH$_2$CH$_2$CO$_2^-$Na$^+$); 1.94–1.40 [m, 6H, —CH$_2$CH$_2$—CO$_2^-$N$^+$, (—CH$_2$C$_4$H$_9$)$_2$]; 1.39–0.97 [m, 12H, HOC(CH$_2$CH$_2$CH$_2$CH$_2$CH$_3$)$_2$]; 0.83 (t, 6H, (—CH$_2$CH$_3$)$_2$; J=5.0 Hz]

Elemental microanalysis: C$_{23}$H$_{35}$O$_3$Na (molecular weight: 382.52)

|  | C | H |
|---|---|---|
| % calculated | 72.22 | 9.22 |
| % found | 72.14 | 9.17 |

EXAMPLE 41

Sodium (5Z)-6-{3-[hydroxy-(1Z)-(4-pent-1-enylphenyl)methyl]-phenyl}hex-5-enoate

Proton NMR spectrum characteristics (300 MHz, CD$_3$OD δ (ppm)):

7.35–7.13 (m, 8H aromatic); 6.40 (d, 1H, ArCH=CH—, J=11.6 Hz); 6.39 (d, 1H, ArCH=CH—, J=11.6 Hz); 5.76 (s, 1H, HOCH—); 5.67 (dt, 1H, —CH=CHCH$_2$—, J=11.3; 7.4 Hz); 5.63 (dt, 1H, —CH=CHCH$_2$—, J=11.5; 7.3 Hz); 2.30 (dt, 2H, —CH=CHCH$_2$—, J=7.2 Hz); 2.29 (dt, 2H, —CH=CHCH$_2$—, J=7.2

Hz); 2.18 (t, 2H, —C$\underline{H}_2$CO$_2^-$Na$^+$, J=7.6 Hz); 1.72 (tt, 2H, —C$\underline{H}_2$CH$_2$CO$_2^-$Na$^+$, J=7.6 Hz); 1.46 (tq, 2H, —C$\underline{H}_2$CH$_3$, J=7.4 Hz); 0.92 (t, 3H, —CH$_2$C$\underline{H}_3$, J=7.3 Hz).

Elemental microanalysis: C$_{24}$H$_{27}$O$_3$Na (molecular weight: 386.47)

|  | C | H |
|---|---|---|
| % calculated | 74.59 | 7.04 |
| % found | 74.21 | 7.22 |

EXAMPLE 42

Sodium (5Z)-6-{3-[hydroxy-(4-pentylphenyl)methyl]-phenyl}hex-5-enoate

Proton NMR spectrum characteristics (90 MHz, CD$_3$OD δ (ppm)):

7.64–6.96 (m, 8H aromatic); 6.38 (d, 1H, —C$\underline{H}$=CHCH$_2$, J=11.7 Hz); 5.88–5.46 (m, 2H, HOC$\underline{H}$—; —CH=C$\underline{H}$CH$_2$—); 2.67–2.03 (m, 6H, ArC$\underline{H}_2$—; —C$\underline{H}_2$CH$_2$CH$_2$CO$_2^-$Na$^+$); 1.94–1.1[m, 8H, —CH$_2$(C$\underline{H}_2$)$_3$CH$_3$; —C$\underline{H}_2$CH$_2$CO$_2^-$Na$^+$]; 0.87 (t, 3H, —CH$_2$C$\underline{H}_3$).

Elemental microanalysis: C$_{24}$H$_{29}$O$_3$Na (molecular weight: 388.49)

|  | C | H |
|---|---|---|
| % calculated | 74.20 | 7.52 |
| % found | 74.33 | 7.78 |

PHARMACOLOGICAL STUDY

EXAMPLE A

Platelet Aggregation Study

The study is carried out on rabbit platelets. After anaesthetizing the animal with sodium pentobarbital (30 mg/kg i.v.), the arterial blood is removed over sodium citrate (0.109M) (1 vol. of citrate per 9 vol. of blood). The plasma rich in platelets (PRP) is obtained by centrifuging (20° C.) at 250 g for 20 minutes. The PRP is centrifuged again (1000 g) for 15 minutes and the platelet sediment is again suspended in a saline solution buffered with tris(hydroxymethyl)aminomethane, containing gelatin (0.2%). After centrifuging again (1000 g; 15 min.), the sediment is again suspended in a physiological solution and stored at room temperature.

The anti-aggregating effect of the products is examined on platelets activated with collagen (2 μl/ml). The platelet aggregation is carried out at 37° C. in siliconised glass tubes using an aggregometer (Coultronics). The platelets are stirred at 1000 rpm. To test the antagonist effect, the PRP is incubated for 3 minutes at 37° C. with the substance to be tested. The collagen is then added (2 μl/ml).

The antagonist effect is measured and the IC$_{50}$ is determined as the concentration of antagonist necessary to produce 50% inhibition of the aggregating responses to collagen.

The results are reproduced in the following table:

| COMPOUND | IC$_{50}$ (μM) |
|---|---|
| Example 4 | 2.2 |
| Example 12 | 20 |
| Example 15 | 21 |
| Example 18 | 30 |
| Example 26 | 1.8 |

EXAMPLE B

Pharmaceutical Composition: Tablets

Formulation for the preparation of 1000 50 mg tablets.

| compound of Example 26 | 50 g |
|---|---|
| wheat starch | 15 g |
| maize starch | 15 g |
| lactose | 65 g |
| magnesium stearate | 2 g |
| silica | 1 g |
| hydroxypropyl cellulose | 2 g |

What is claimed is:

1. A compound selected from those of formula (I):

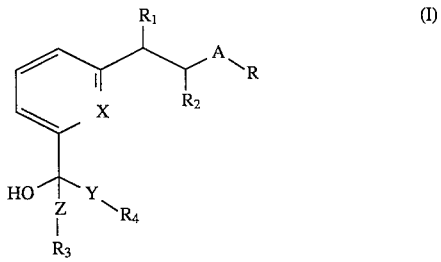

wherein:

A represents a divalent hydrocarbon radical having 2 to 10 carbon atoms inclusive in straight or branched chain and optionally containing one or more unsaturations in the form of double and/or triple bonds, R is selected from fluorine, chlorine, bromine and iodine, —OR', —COOR', —COR', P(O)(OR')$_2$, —CH=N—OR', —CONHR', —CH=NR", —CH=NAr, NHSO$_2$Ar, —CON(OH)R', —NHR', —NHCOR', —CH=N—NHAr,

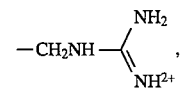

and optionally substituted imidazolyl, pyrazolyl or tetrazolyl,

R' is selected from hydrogen and straight-chain or branched alkyl having 1 to 6 carbon atoms inclusive, R" represents straight-chain or branched alkyl having 1 to 6 carbon atoms inclusive, Ar represents optionally substituted aryl selected from phenyl and naphthyl, R$_1$ and R$_2$ each represents hydrogen or together form a bond, R$_3$ is selected from hydrogen and alkyl having 2 to 10 carbon atoms inclusive in straight or branched chain, R$_4$ represents a hydrocarbon radical having 2 to 10 carbon atoms inclusive in straight or branched chain and optionally containing one or more unsaturations in the form of double and/or triple bonds, X is selected from CH and nitrogen, Y and Z each represents, independently of the other, a valency bond or para-phenylene, it being understood that the expression "optionally substituted" indicates that the radical concerned may optionally be substituted by one or more groups selected from chlorine, fluorine, bromine, iodine, amino, alkylamino, dialkylamino, nitro, cyano, alkyl, alkoxy, acyl, acyloxy, carboxy, alkoxycarbonyl, amido and carboxamido, its stereoisomers, its possible N-oxides, or its pharmaceutically-acceptable addition salts with an acid or a base.

2. A compound selected from those of claim 1, wherein X represents CH, its stereoisomers, N-oxides or pharmaceutically-acceptable addition salts with an acid or a base.

3. A compound selected from those of claim 1, wherein X represents nitrogen, its stereoisomers, N-oxides or pharmaceutically-acceptable addition salts with an acid or a base.

4. A compound selected from those of claim 1, wherein Z represents a valency bond, its stereoisomers, N-oxides or pharmaceutically-acceptable addition salts with an acid or a base.

5. A compound selected from those of claim 1, wherein Y represents a valency bond, its stereoisomers, N-oxides or pharmaceutically-acceptable addition salts with an acid or a base.

6. A compound selected from those of claim 1, wherein $R_3$ represents hydrogen, its stereoisomers, N-oxides or pharmaceutically-acceptable addition salts with an acid or a base.

7. A compound of claim 1, which is sodium (5Z)-6-{3-[(3Z)-(1-hydroxynon-3-en-1-yl)]phenyl}hex-5-enoate or a stereoisomer thereof.

8. A method for treating a mammal afflicted with a disease requiring a platelet antiaggregating agent comprising the step of administering to said mammal an amount of a compound of claim 1 which is effective for alleviation of said disease.

9. A pharmaceutical composition useful in the claim 8 method comprising an effective platelet antiaggregating amount of a compound as claimed in claim 1, together with one or more pharmaceutically-acceptable excipients or vehicles.

* * * * *

UNITED STATES PATENT AND TRADEMARK OFFICE
CERTIFICATE OF CORRECTION

PATENT NO. : 5,599,975  
DATED : February 4, 1997  
INVENTOR(S) : R. Gree; A.M. Hachem; D. Gree; Y.L. Floc'h; Y. Rolland; S. Simonet; T. Verbeuren Page 1 of 2

It is certified that error appears in the above-indentified patent and that said Letters Patent is hereby corrected as shown below:

Column 1, line 11: "(1 5-HETE," should read -- (15-HETE, --.

Column 2, line 65: "$R_4A$)," should read -- $R_{4A}$), --.

Column 11, line 28: "Hhd 2N-R''," should read -- $H_2N-R''$, --.

Column 17, line 27: "$-CH_2H_3$, J=6.0 Hz)" should read -- $-CH_2CH_3$, J=6.0 Hz) --.

Column 18, line 45: "[m, 6H, $-CH_2(CH_2)_3$];" should read -- [m, 6H, $-CH_2(CH_2)_3CH_3$]; --.

Column 28, line 45: At the end of the line, "$4.4 \times 10^-$" should read -- $4.4 \times 10^{-3} M$ --.

Column 28, line 46: Delete "3M" at the beginning of the line.

Column 29, line 17: "$3.2 \times 10^-$" at the end of the line should read -- $3.2 \times 10^{-3} M$ --.

Column 29, line 18: Delete "3M" at the beginning of the line.

UNITED STATES PATENT AND TRADEMARK OFFICE
CERTIFICATE OF CORRECTION

PATENT NO. : 5,599,975
DATED : February 4, 1997
INVENTOR(S) : R. Gree; A.M. Hachem; D. Gree; Y.L. Floc'h; Y. Rolland; S. Simonet; T. Verbeuren It is certified that error appears in the above-indentified patent and that said Letters Patent is hereby corrected as shown below:

Column 32, line 30: "$-CH_2CH_2-CO_2-N^+$," should read -- $-CH_2CH_2-CO_2-Na^+$, --.

Column 33, line 24: "1.94-1.1[m," should read -- 1.94-1.14[m, --.

Column 35, line 11: Insert a -- , -- (comma) at the end of the line, after "amido".

Column 36, lines 18 and 19: After the word "useful", <u>Insert</u> -- as a platelet antiaggregation agent --; and <u>Delete</u> "in the claim 8 method".

Signed and Sealed this

Twenty-second Day of April, 1997

*Attest:*

BRUCE LEHMAN

*Commissioner of Patents and Trademarks*

*Attesting Officer*